US009101395B2

(12) United States Patent
Gutierrez et al.

(10) Patent No.: US 9,101,395 B2
(45) Date of Patent: Aug. 11, 2015

(54) METHOD AND SYSTEM FOR BRACHYTHERAPY (75) Inventors: Luis Felipe Gutierrez, Jersey City, NJ (US); Guy Shechter, Briarcliff Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 286 days.

(21) Appl. No.: 12/992,905

(22) PCT Filed: Jun. 12, 2009

(86) PCT No.: PCT/IB2009/052522
§ 371 (c)(1),
(2), (4) Date: Nov. 16, 2010

(87) PCT Pub. No.: WO2009/156893
PCT Pub. Date: Dec. 30, 2009

(65) Prior Publication Data
US 2011/0166410 A1 Jul. 7, 2011

Related U.S. Application Data (60) Provisional application No. 61/075,483, filed on Jun. 25, 2008.

(51) Int. Cl.
*A61N 5/00* (2006.01)
*A61B 19/00* (2006.01)
*A61N 5/10* (2006.01)

(52) U.S. Cl.
CPC .......... *A61B 19/5244* (2013.01); *A61N 5/1015* (2013.01); *A61B 2019/5251* (2013.01);
(Continued)

(58) Field of Classification Search
USPC ...................... 600/8, 1–7, 407, 424
See application file for complete search history.

(56) References Cited

U.S. PATENT DOCUMENTS 5,840,008 A 11/1998 Klein et al.
6,147,480 A 11/2000 Osadchy et al.
(Continued)

FOREIGN PATENT DOCUMENTS

GB 2429130 2/2007
WO WO2007145965 12/2007
(Continued)

OTHER PUBLICATIONS

S. Miller et al., "An Implementation of a Virtual Reality Interstitial Brachytherapy System", IEEE 1998, Dept. of Electrical and Computer Engineering, and Dept. of Medical Physics, Univ. of Manitoba, Canada, pp. 870-873.
(Continued)

*Primary Examiner* — Jacqueline Cheng
*Assistant Examiner* — Eileen Hyde (57) ABSTRACT A brachytherapy system for a target region includes an applicator having a plurality of channels that are hollow, where the applicator is implanted in the target region. The system further includes a tracking device, a tracking signal generator to generate a signal received by the tracking device, and a processor. The tracking device has a size and shape to be advanced and retracted through at least a portion of the plurality of channels. The processor can determine a position of one or more of the plurality of channels based on a movement of the tracking device. The processor can further determine the location of the plurality of channels in the images based on the position measurements from the tracking device.

22 Claims, 4 Drawing Sheets (52) U.S. Cl.
CPC . *A61B2019/5272* (2013.01); *A61B 2019/5287* (2013.01); *A61B 2019/5289* (2013.01); *A61B 2019/5408* (2013.01); *A61N 2005/1018* (2013.01)

(56) References Cited

U.S. PATENT DOCUMENTS

| | | | |
|---|---|---|---|
| 6,438,401 B1* | 8/2002 | Cheng et al. | 600/407 |
| 6,454,696 B1* | 9/2002 | Kindlein et al. | 600/7 |
| 2006/0094923 A1* | 5/2006 | Mate | 600/3 |
| 2007/0066880 A1* | 3/2007 | Lee et al. | 600/407 |
| 2007/0232882 A1* | 10/2007 | Glossop et al. | 600/407 |
| 2008/0091055 A1* | 4/2008 | Nguyen et al. | 600/7 |
| 2008/0269596 A1* | 10/2008 | Revie et al. | 600/424 |
| 2010/0312038 A1* | 12/2010 | Shechter | 600/3 |

FOREIGN PATENT DOCUMENTS

| | | |
|---|---|---|
| WO | WO2008045812 | 4/2008 |
| WO | WO2009053897 | 4/2009 |

OTHER PUBLICATIONS

Y. Watanabe et al., "A System for Nonradiographic Source Localization and Real-Time Planning of Intraoperative High Dose Rate Brachytherapy", Med, Phys., vol. 24, No. 12, Dec. 1997, pp. 2014-2023.

Wood, B.J. et al. "Technologies for guidance of radiofrequency ablation in the multimodality interventional suite of the future", J Vasc Intery Radiol. Jan. 2007: 18(1 Pt 1): 9-24.

Wesarg, S. et al. "Accuracy of needle implantation in brachytherapy using a medical AR system—a phantom study", Proc. SPIE5367, Medical Imaging 2004, Visualization, Image-Guided procedures, and Display, 341 (May 5, 2004).

Krucker, J. et al. "Electromagnetic tracking for thermal ablation and biopsy guidance: clinical evaluation of spatial accuracy", J. Vasc Intery Radiol. Sep. 2007; 18(9): 1141-1150.

Strassmann, G. et al. "Navigation system for interstitial brachytherapy", Radiotherapy and Oncology 56 (2000) 49-57.

Seiler, P.G. et al. "A novel tracking technique for the continuous precise measurement of tumour positions in conformal radiotherapy", Phys. Med. Biol. 45 (2000) N103-N110, UK.

The NDI Aurora Electromagnetic Tracking System, Northern Digital Inc., 2005.

Wood, B.J. et al. "Navigation with electromagnetic tracking for interventional radiology procedures: A feasibility study", J Vasc Interv Radiol. Apr. 2005: 16(4): 493-505.

European Patent Office, Communication of a notice of opposition. Sep. 29, 2014. Application No./Patent No. 09769703.1-1652/2293844.

* cited by examiner

METHOD AND SYSTEM FOR BRACHYTHERAPY

This application is a national stage application under 35 U.S.C. §371 of International Application No. PCT/IB2009/052522 filed on Jun. 12, 2009, which claims priority to U.S. Provisional Application No, 61/075,483 filed on Jun. 25, 2008.

The present application relates to the therapeutic arts, in particular in conjunction with high dose rate (HDR) brachytherapy and will be described with particular reference thereto. However, it is to be appreciated that the invention will also find application in conjunction with other therapeutic treatments, such as low dose brachytherapy, pulsed dose brachytherapy, radio-frequency ablation, cryo-ablation, microwave ablation, laser ablation, positioning other treatment sources, and the like.

Cancer is often treated with a combination of therapies, such as surgery, chemotherapy, radiation therapy, and the like. For example, a tumor is often removed surgically, after which the patient is treated with chemotherapy or radiation to kill any cancerous cells which were not removed. In one radiation treatment, a beam of x-rays from a linear accelerator are directed through a target region(s). By contrast, in brachytherapy, a radioactive source or seed(s) is inserted into a target region to irradiate the target region from within.

In HDR brachytherapy, an applicator is positioned in the patient, extending through the target area to be irradiated. An applicator may be one catheter, a multiplicity of separable channels, a device containing several channels, one or more needles, or an organ-specific design. A high dose rate source, e.g., an Iridium-192 pellet or seed is moved through the applicator on the end of a wire and dwells at one or more positions for a planned period of time. This treatment is repeated, typically, once or twice per day over a period of several days.

In the example of treating breast cancer, following a lumpectomy, an applicator is surgically implanted into the target region to be irradiated. A CT scan is conducted to generate a high resolution image of the applicator and tissue in the target region. This image is used for a brachytherapy planning session to plan where along the applicator the source will be positioned and for how long.

The planned brachytherapy treatment is then applied once or twice a day for several days. Particularly with soft tissue such as the breast, there is the possibility that the applicator can shift relative to the treated tissue. To assure that the applicator is in the proper position and that the planned treatment is being delivered, a CT scan and accompanying segmenting of the applicator in the images is conducted prior to each brachytherapy session. This can be a time consuming and laborious process.

The Summary is provided to comply with 37 C.F.R. §1.73, requiring a summary of the invention briefly indicating the nature and substance of the invention. It is submitted with the understanding that it will not be used to interpret or limit the scope or meaning of the claims.

In accordance with one aspect of the exemplary embodiments, a method of brachytherapy can include positioning an applicator into a target region where the applicator has a plurality of hollow channels, moving a tracking device through at least a portion of the plurality of channels, obtaining a position of one or more of the plurality of channels based on the movement of the tracking device, and generating a brachytherapy plan for administering a radiation dose based on the position of the one or more of the plurality of channels.

In accordance with another aspect of the exemplary embodiments, a computer-readable storage medium can include computer-executable code stored therein, where the computer-executable code is configured to cause a computing device in which the computer-readable storage medium is loaded to execute the steps of obtaining a position of one or more of a plurality of channels of an applicator with respect to a target region based on a tracking device, where the applicator is positioned in the target region, where the tracking device is moved through the one or more of the plurality of channels, and generating at least a portion of a brachytherapy plan for administering a radiation dose based on the position of the one or more of the plurality of catheters.

In accordance with another aspect of the exemplary embodiments, a brachytherapy system for a target region can include an applicator having a plurality of hollow channels, a tracking device, a tracking signal generator to generate a signal received by the tracking device, and a processor. The tracking device can have a size and shape to be advanced and retracted through at least a portion of the plurality of channels. The processor can determine a position of one or more of the plurality of channels based on a movement of the tracking device.

The exemplary embodiments described herein have a number of advantages over contemporary systems and processes, including a reduction of radiation exposure and assured accuracy of a planned brachytherapy. Additionally, the system and method described herein can be retrofitted to existing applicators, and does not need to be manufactured with tracking systems incorporated therein. Still further advantages and benefits will become apparent to those of ordinary skill in the art upon reading and understanding the following detailed description.

The above-described and other features and advantages of the present disclosure will be appreciated and understood by those skilled in the art from the following detailed description, drawings, and appended claims.

The exemplary embodiments of the present disclosure are described with respect to high dose rate (HDR) brachytherapy of a human. It should be understood by one of ordinary skill in the art that the exemplary embodiments of the present disclosure can be applied to other types of brachytherapy and other portions of the body, whether human or animal. The use of the method and system of the exemplary embodiments of the present disclosure can be adapted for application to other types of applicators. The use of the method and system of the exemplary embodiments of the present disclosure can be adapted for application to other types of therapies, including but not limited to radiofrequency ablation, cryo-ablation, microwave ablation, and laser ablation.

Referring to the drawings, and in particular to FIGS. 1-5, a brachytherapy system 10 can have an applicator 100 with a plurality of hollow channels or cannulae 110 extending from a radiation seed receiving end 105 of the applicator to a closed tip 115 at an opposite end of the applicator. It should be understood by one of ordinary skill in the art that the particular shape of the channels 110 can vary, and can be struts, catheters, tubes or other structures which allow for guiding of a radioactive seed therealong. A rotation knob 120 or other actuator can be operably connected to the hollow channels 110 so that the channels can be selectively radially expanded (e.g., bowing). For example, the channels 110 can be flexible tubes that are axially compressed through use of the rotation knob 120 resulting in the channels deforming radially outwardly.

Figure 1:
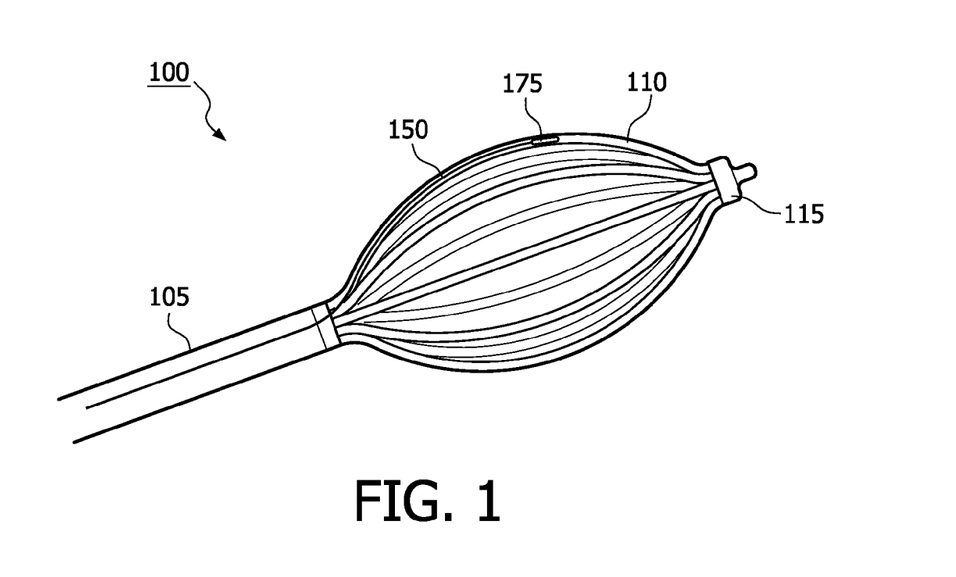
FIG. 1 is a schematic illustration of an applicator for use with a brachytherapy system of one exemplary embodiment.
Figure 2:
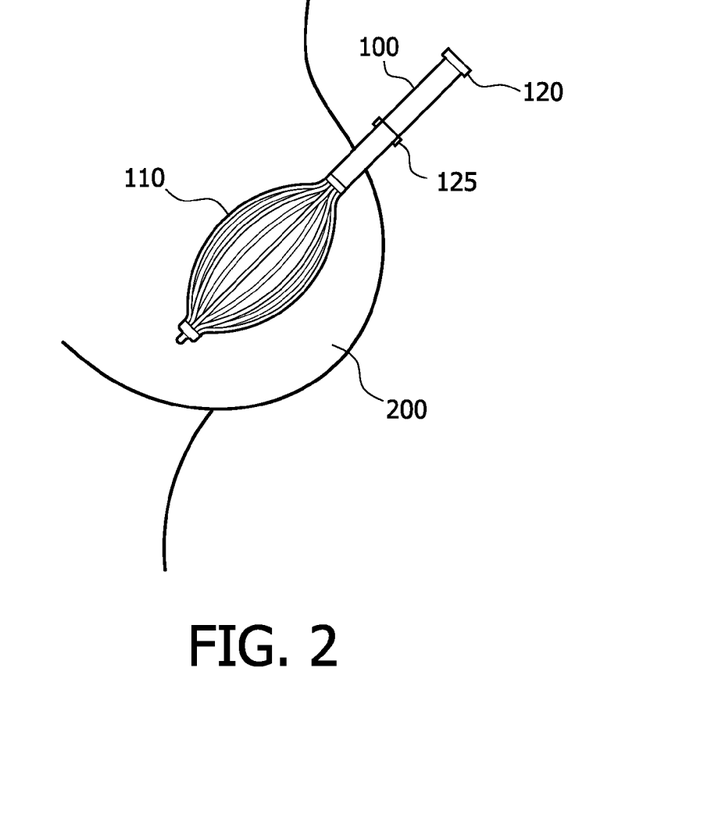
FIG. 2 depicts a first view of the brachytherapy applicator of FIG. 1 implanted into a target anatomy.
Figure 3:
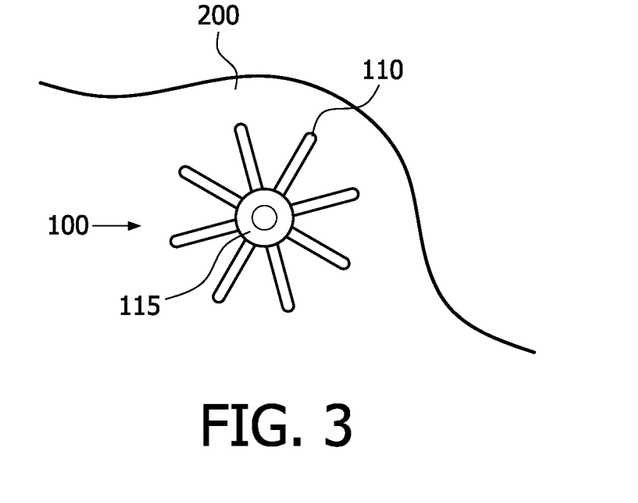
FIG. 3 depicts a second view of the brachytherapy applicator of FIG. 1 implanted into the target anatomy.
Figure 4:
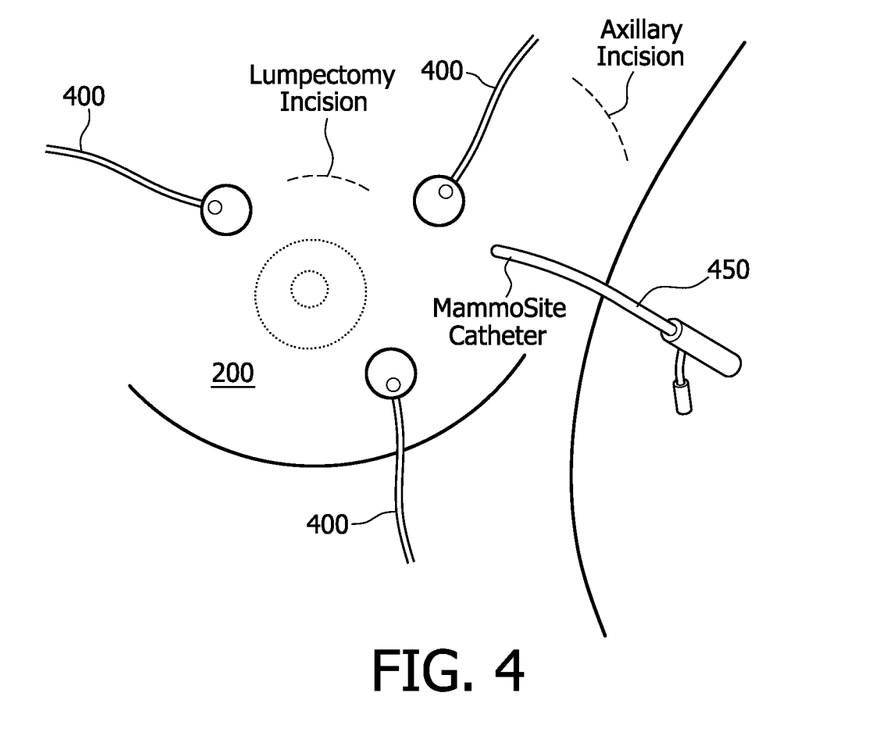
FIG. 4 is a schematic illustration of the targeted anatomy with a portion of the brachytherapy system positioned thereon.

An expansion mechanism, such as a draw rod, can be operated via the actuator 120 to expand the inserted head portion of the applicator 100, e.g., to bring the tip 115 and a compressor ring 125 towards each other, causing the channels in the head portion to bow outwardly. The channels can be expanded to an appropriate bulbous configuration to bring the seed delivery paths defined by the hollow channels adjacent to the tissue or other target anatomy to be irradiated. One such applicator having flexible, deformable channels for this treatment is a Cianna SAVI™ HDR applicator available from Cianna Medical of Aliso Veijo, Calif. As will be described later, the outward deformation allows the applicator 10 to fill a void in the target anatomy so as to efficiently deliver treatment thereto.

The brachytherapy system 10 can include a moveable tracking sensor 175. The sensor 175 can be an electromagnetic sensor that receives EM signals generated by a field generator 180 or the like. In one embodiment, the EM sensor 175 can be connected to a wire or other semi-rigid cable 150 that allows the sensor to be moved through each of the channels 110 via pushing and pulling forces. Various types of EM tracking systems can be utilized.

In one embodiment, the field generator 180 can have a plurality of antennas at different orientations. The sensor 175 can pick up the signals from the antennas at the various orientations along various positions of the channels 110. From their relative signal characteristics, e.g., relative signal strength, relative phase, etc., the location of the sensor 175 relative to the antennas can be determined. In another embodiment, the sensor 175 can have receiving coils or antennas with different orientations. In one embodiment, the sensor 175 can be in communication with a processor 550 of the imaging system 500 by wires running through or along the applicator 100, such as along the wire 150. In another embodiment, a wireless communication path can be used. Other types of applicators and other types of tracking systems are also contemplated.

In one embodiment, the tracking system can use various tracking components, such as those available from Traxtal Inc. or Northern Digital Inc. As another example, the moveable tracking sensor 175 can utilize optical tracking techniques and components, such as available in the Northern Digital Optotrak Certus Motion Capture System. Other techniques and components can be used as a location sensor or transmitter and a location monitor or receiver, including ultrasound techniques and components.

Figure 6:
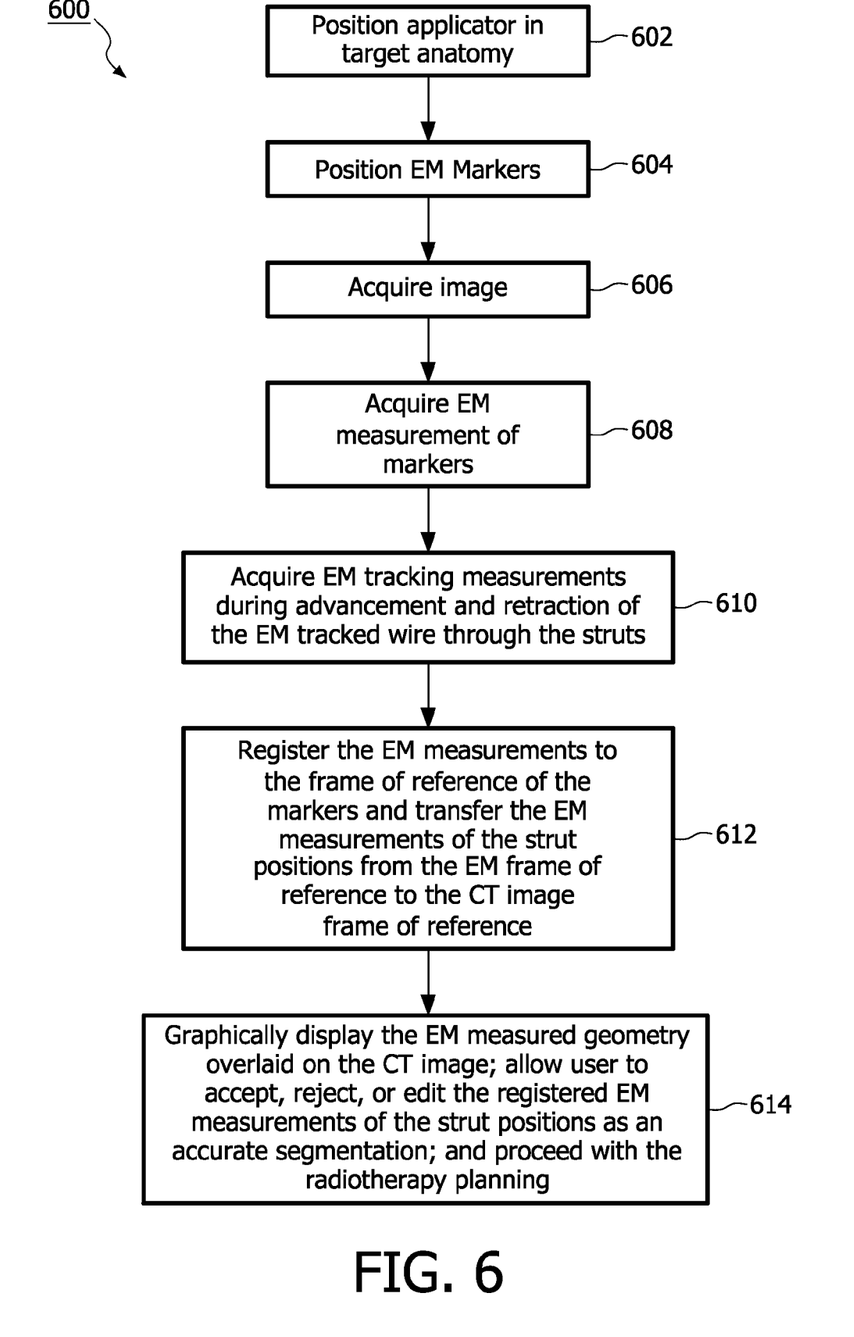
FIG. 6 is a method that can be used by the system of FIGS. 1-5 for performing brachytherapy.

Referrer additionally to FIG, 6, a method of brachytherapy is generally illustrated by reference numeral 600, The method 600 can be employed for radiation treatment following various types of procedures, such as after lumpectomy surgery is performed to remove a cancerous or potentially cancerous lump or other undesired tissue from the target anatomy 200 which is shown situated on a bed or other platform 520. After the surgery, in step 602 the applicator 100 can be inserted in its collapsed state through an incision or other point of entry for the target anatomy, including through catheter 450 or the like. The collapsed state of the applicator 100 can include each of the hollow channels 110 extending parallel to, and in proximity with, each other to minimize the cross-section of the applicator. In one embodiment, the applicator 100 can be positioned using an ultrasonic guidance system to place the applicator in the selected position, typically with the head portion in the volume vacated by the lump. Other guidance systems can also be utilized, including other imaging techniques. Using the actuator 120 or some other expansion mechanism, channels 110 of the applicator 100 can be expanded to an appropriate bulbous configuration to bring the seed delivery paths defined by the hollow channels adjacent to the tissue that is to be irradiated.

After insertion and expansion of the applicator, in step 604 a plurality of markers or fiducials 400, e.g., one marker or more, can be mounted on the targeted anatomy 200 in proximity to the implanted applicator 100. Each marker 400 can include an electromagnetic sensor unit and can be imageable by a high resolution imaging modality, such as CT scanner 500.

Figure 5:
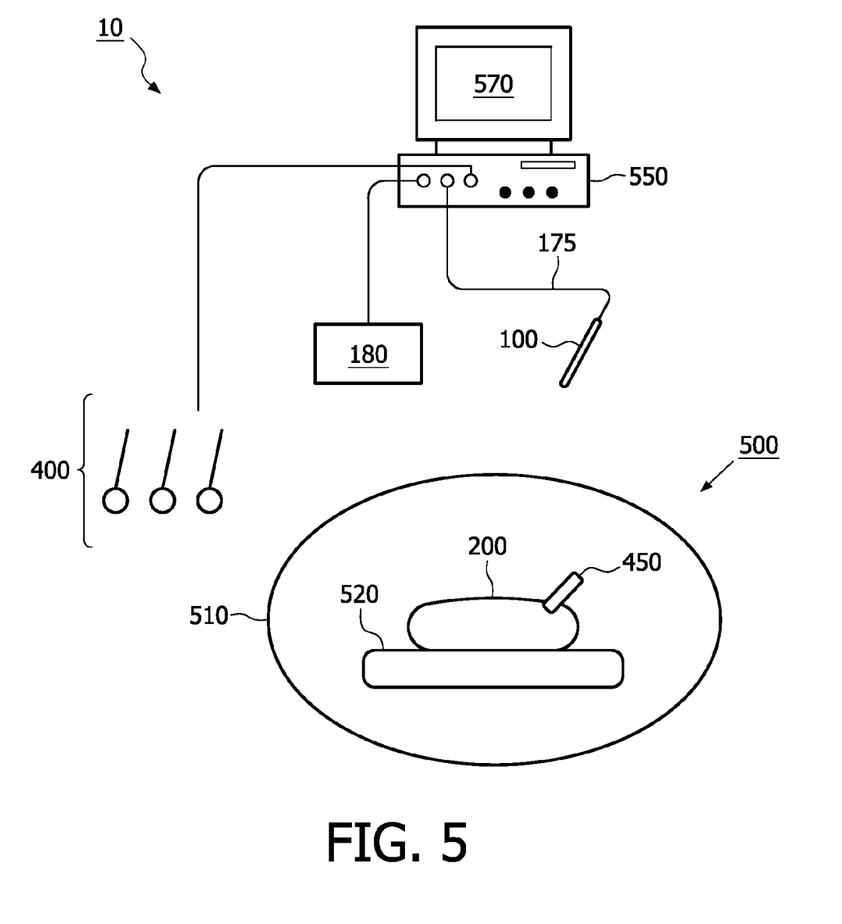
FIG. 5 is a schematic illustration of the brachytherapy system.

In step 606, a high resolution image of the target region 200 including the applicator 100 and the surrounding tissue can be generated by the CT scanner 500 and stored in a CT image memory. A closed CT scanning device 510 is shown in FIG. 5 for illustrative purposes, but the present disclosure contemplates the use of various imaging devices, including a moving C-arm device or MRI.

In step 608, the position and orientation of each of the markers 400 is obtained using the tracking system, such as the EM tracking system and the field generator 180. For example, EM signals can be generated by the field generator 180 and received by the markers 400 that are mounted to the target anatomy 200. A processor 550 can determine the position and orientation of the markers 400 from the acquired EM data. As described above, where other tracking techniques are utilized, such as ultrasound or optics, then the tracking system can use those modalities to take measurements of the position and orientation of the markers 400.

In step 610, the EM sensor 175 or other moveable tracking device can be positioned in one of the channels 110 and advanced therealong while acquiring EM or other tracking measurements. This procedure can be repeated for each of the channels 110 and can be performed through advancement and/or retraction of the sensor 175, such as through use of the wire 150. The wire 150 can be manually advanced and retracted through the channels 110. However, the present disclosure contemplates an actuator or other power for advancing and retracting the wire 150 being operably connected to the wire, which can be advanced and/or retracted under a controlled speed.

Method 600 can utilize the EM data for segmentation of the CT images. In step 612, a user can identify the EM tracked markers 400 in the CT image, and use this information to register the EM measurements to the frame of reference of the CT image. The resulting registration can be utilized to transfer the EM measurements of the positions of the channels 110 from the EM frame of reference to the CT image frame of reference. In another embodiment, system 10 can register the EM measurements to the frame of reference of the CT image without user intervention, such as through use of the controlled speed of the movement of the wire 150. In step 614, system 10 can graphically display the EM measured geometry overlaid onto the CT image, such as through use of display 570. The user can then accept, reject, or edit the registered EM measurements of the strut positions as an accurate segmentation, and then proceed with the radiotherapy planning.

It should be understood that the use of markers 400 is one technique for localizing the channels 110 in the image based in part on the tracking measurement information. The present disclosure contemplates other techniques being utilized in addition to, or as an alternative of, the markers 400. For example, the exemplary embodiments can utilize image correlation or processing algorithms for localization. For instance, one or more features that appear in the image and have a known position can be utilized by the image correlation algorithms, such as portions of the applicator 100.

In one embodiment, processor 550 can determine the relative locations of the sensor 175 for various positions along the channels 110 relative to the patient mounted markers 400 and can generate a sensor map. Where the markers 400 are also imaged in the CT image, the positions of the sensor 175 along the channels 110 relative to the markers can also be known in the coordinate system of the CT scanner and the CT image which it generates. In another embodiment, the various positions or locations of the sensor 175 as it travels through the channels 110 from the sensor map can be superimposed onto the CT image to generate a combined image, which can be stored in a planning session memory.

In one embodiment, the information obtained from the imaging and EM tracking, such as the combined image, can be utilized in a brachytherapy planning session to plan the brachytherapy. This planning session can involve determining into which of the channels a radioactive seed will be placed; the position along the strut for placement of the seed; and how long the seed will remain at that position. For example, each radioactive seed can generate a known dose per unit time in each of a plurality of generally-spherical regions surrounding the seed. By positioning the radioactive seed in different locations along the channels 110 for different periods of time, the total radiation dose in regions of the surrounding tissue 200 can be determined. In the planning session, the desired dose to be delivered in each of one or more designated surrounding tissue regions can be determined by the treating oncologist and the positions and duration of the seed(s) can be calculated in order to match the delivered dose distribution to the desired dose distribution. In one embodiment, the calculations can be performed by processor 550 which is suitably programmed to generate a treatment plan and optimize the positioning of seeds, such as based on an oncologist's selected dose distribution inputted into a graphic user interface of the processor.

Various methods of brachytherapy can then be employed based on the radiotherapy plan that has been developed through use of system 10. For instance, an afterloader can be programmed with the planned therapy session, loaded with the appropriate radioactive seed(s) and attached to a loading end of the applicator 100. In one embodiment, each seed can carry its own EM sensor or other tracking device to confirm positioning of the seed. The afterloader can move the seed through each of the selected channels 110 to each of the calculated positions or locations along the channels for each of the calculated durations. In another embodiment, the seeds can be moved into position along the channels using other devices and other information, such as measurements of the moving device operably connected to the seed (e.g., a length that a wire has been extended into the applicator).

Brachytherapy sessions can be administered multiple times during a day for several days, with the applicator remaining implanted during the sessions. In one embodiment, method 600 or portions thereof can be repeated to confirm that the applicator has not become misaligned. In another embodiment, the processor 550 can compare the alignment data (i.e., recently obtained strut positions) with the original strut positions to determine if misalignment of the applicator 100 within the target anatomy 200 has occurred. If the processor 550 determines that the positions have changed, one option is to attempt to reposition the applicator 100 as additional measurements of the EM sensor 175 is taken, trying to bring the applicator back or as close as possible to its original position and orientation.

If the applicator 100 is not in the original position at which the therapy was planned, a transform can be determined by the processor 550 between the current and original location of the applicator relative to the markers 400 and the targeted anatomy 200. This transform can be used by the processor to operate on the planning image, such as from a planning image memory, to shift the relative location of the applicator 100 and the target region 200 in accordance with the transform to form a transformed therapy planning image. This shifted information can be used by the processor 550 to generate a new brachytherapy plan. The new brachytherapy plan can be loaded into the afterloader and the next brachytherapy session can be commenced.

In one embodiment, during the dose delivery, the positions of the channels 110 and the seed can be tracked during dose delivery by an EM sensor or other tracking device coupled to the seed. For instance, the target tissue 200 can be divided into three-dimensional (3D) subregions. The EM tracked seed location can be mapped into the 3D subregions, and the cumulative dose in each subregion can be continuously or intermittently updated or incremented based on time and distance from the source, which allows the delivered dose to be monitored by processor 550 and/or the clinician. If a deviation from the brachytherapy plan is detected, an updated dose plan can be generated based on the deviation (e.g., change duration for the seed at the next position and so forth) and/or the treatment can be halted. Performing tracking of the channels and the seed during a brachytherapy session assures that there is no motion of the applicator during the session and, if any motion occurs, the treatment planning calculator can recalculate the brachytherapy plan in real time. Feedback of the seed position from a tracking device coupled to the seed can also be used to create a record of the treatment plan or a radiation map showing the radiation actually delivered in each session.

In one embodiment, the imaging of the applicator 100 after surgical placement can be performed using MRI or ultrasound (e.g., 3D US) imaging. The present disclosure also contemplates using automatic identification of the EM tracked fiducial markers 400 in the image (CT, MRI and/or US). In one embodiment, the system 10 can graphically display the EM measured geometry overlaid on the image (CT, MRI and/or US), where the user can selectively blend between the EM geometry and the image. In another embodiment, the system 10 can utilize registered EM measurements of the strut positions to initialize automatic refinement of the segmentation process.

Although described with reference to the breast, other brachytherapy treatments are also contemplated such as prostate, head, neck, and gynecological.

The invention, including the steps of the methodologies described above, can be realized in hardware, software, or a combination of hardware and software. The invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention, including the steps of the methodologies described above, can be embedded in a computer program product. The computer program product can comprise a computer-readable storage medium in which is embedded a computer program comprising computer-executable code for directing a computing device or computer-based system to perform the various procedures, processes and methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed as the best mode contemplated for carrying out this invention, but that the invention will include all embodiments falling within the scope of the appended claims.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

What is claimed is:

1. A method of brachytherapy, the method comprising the acts of:
positioning an applicator into a target region at an initial position in accordance with an initial brachytherapy plan, the applicator having a plurality of hollow channels subject to a shifting of position during use;
generating signals by a generator;
moving a tracking device through at least a portion of the plurality of hollow channels, wherein the tracking device includes more than one receiving coil or antenna configured to receive signals from the generator;
acquiring position measurements from the tracking device based on characteristics of the signals received by the tracking device during movement of the tracking device through the at least a portion of the plurality of hollow channels;
obtaining a shifted position of one or more of the plurality of hollow channels by comparing the position measurements acquired during the movement of the tracking device through the at least a portion of the plurality of hollow channels to the initial position;
localizing the shifted position of the one or more of the plurality of hollow channels in an image using the position measurements from the tracking device;
positioning a radioactive seed in one of the plurality of hollow channels to provide a radiation dose, wherein a seed sensor is coupled to the radioactive seed to confirm a seed position of the radioactive seed, and wherein the seed sensor is provided in addition to the tracking device; and
updating the initial brachytherapy plan by a processor for administering the radiation dose based on the shifted position of the one or more of the plurality of hollow channels.

2. The method of claim 1, further comprising positioning one or more markers in proximity to the target region and connected to an external portion of the target region, wherein the shifted position of the one or more of the plurality of hollow channels is localized based at least in part on the one or more markers, wherein the one or more markers are imageable.

3. The method of claim 1, further comprising:
positioning the tracking device at an end of a wire; and
moving the tracking device using the wire.

4. The method of claim 3, wherein the brachytherapy plan comprises the seed position of the radioactive seed with respect to one of the plurality of hollow channels and a duration at the seed position.

5. The method of claim 1, wherein the target region is one of a breast, prostate, head, neck and gynecological area.

6. The method of claim 1, further comprising the act of applying image correlation algorithms to localize the shifted position of the one or more of the plurality of hollow channels in the image based in part on one or more features shown in the image.

7. The method of claim 1, further comprising the act of performing at least one of computed tomography, magnetic resonance imaging, and ultrasound imaging to acquire the image.

8. The method of claim 1, further comprising the act of displaying the image with a geometry representative of the one or more of the plurality of hollow channels overlaid thereon, wherein the geometry representative is determined from the signals generated by the generator and received by the tracking device and markers that include electromagnetic sensor units configured to receive the signals from the generator for determination of positions and orientations of the markers, wherein the markers are connected to an external portion of the target region.

9. The method of claim 1, wherein the plurality of hollow channels are expandable by bowing outwardly, and wherein the generating act includes determining which of the plurality of hollow channels receives the radioactive seed based on the position of the one or more of the plurality of channels.

10. The method of claim 1, wherein the generator has a plurality of antennas at different orientations, and wherein the obtaining act obtains the shifted position of the one or more of the plurality of hollow channels based on the position measurements acquired during the movement of the tracking device and based on positions and orientations of markers connected to an external portion of the target region, wherein at least one of the markers includes an electromagnetic sensor unit configured to receive the signals from the generator for determination of the positions and the orientations of markers, and wherein the markers are imageable.

11. The method of claim 1, wherein receiving coils or antennas of the more than one receiving coil or antenna of the tracking device have different orientations.

12. The method of claim 1, further comprising the acts of:
displaying a measured geometry obtained from position measurements overlaid on the image to form a combined image; and
presenting a user with an option to accept, reject, or edit the combined image and to selectively blend between the measured geometry and the image,
wherein the combined image includes positions tracking device as it travels through the at least a portion of the plurality of hollow channels.

13. The method of claim 1, further comprising the act of selectively expanding the plurality of hollow channels by rotating a knob.

14. A non-transitory computer-readable storage medium in which computer-executable code is stored, the computer-executable code configured to cause a computing device in which the non-transitory computer-readable storage medium is loaded to execute the acts of:
moving a tracking device through at least a portion of hollow channels of an applicator that are subject to a shifting of position during use, wherein the tracking device includes more than one receiving coil or antenna configured to receive signals from a generator;
acquiring position measurements from the tracking device based on characteristics of the signals received by the tracking device during movement of the tracking device through the at least a portion of the plurality of hollow channels;
obtaining a shifted position of one or more of the hollow channels with respect to an initial position of the of one or more of the hollow channels in a target region by comparing the position measurements acquired during the movement of the tracking device through the at least a portion of the plurality of hollow channels to the initial position;
positioning a radioactive seed in one of the hollow channels to provide a radiation dose, wherein a seed sensor is coupled to the radioactive seed to confirm a seed position of the radioactive seed, and wherein the seed sensor is provided in addition to the tracking device; and
generating at least a portion of a brachytherapy plan for administering the radiation dose based on the position of the one or more of the hollow channels.

15. The non-transitory computer-readable storage medium of claim 14, wherein the shifted position is obtained based on the position measurements and based on a position and an orientation of a marker determined from signals received by the marker from the generator, wherein the marker is connected to an external portion of the target region and includes an electromagnetic sensor unit configured to receive the signals from the generator for determination of the position and the orientation of the marker, and wherein the channels are expandable channels by bowing outwardly.

16. The non-transitory computer-readable storage medium of claim 15, further comprising computer-executable code for causing the computing device to:
acquire an image of the target region having the marker in the image; and
register the position of the one or more of the hollow channels based on a location of the marker in the image.

17. The non-transitory computer-readable storage medium of claim 16, further comprising computer-executable code for causing the computing device to perform at least one of computed tomography, magnetic resonance imaging, and ultrasound imaging to acquire the image of the target region.

18. The non-transitory computer-readable storage medium of claim 16, further comprising computer-executable code for causing the computing device to display the image with a geometry representative of the one or more of the hollow channels overlaid thereon.

19. A brachytherapy system for a target region, the system comprising:
an applicator having a plurality of channels that are hollow and expandable and are subject to a shifting of position during use, the applicator being implantable in the target region at an initial position in accordance with an initial brachytherapy plan;
a tracking signal generator configured to generate signals;
a tracking device that includes more than one receiving coil or antenna configured to receive the signals from the tracking signal generator;
a seed sensor coupled to a radioactive seed to confirm a seed position of the radioactive seed in one channel of the plurality of channels, wherein the seed sensor is provided in addition to the tracking device; and
a processor,
wherein the tracking device has a size and shape to be advanced and retracted through at least a portion of the plurality of channels,
wherein the processor is configured to:
acquire position measurements from the tracking device during movement of the tracking device through the at least a portion of the plurality of channels, and determine a shifted position of one or more of the plurality of channels by comparing the position measurements acquired during the movement of the tracking device to the initial position,
determine a location of one or more of the plurality of channels in an image based on the position measurement from the tracking device during the movement of the tracking device through the at least a portion of the plurality of hollow channels,
determine the seed position of the radioactive seed in the one channel based on information from the seed sensor; and
updating the initial brachytherapy plan for administering a radiation dose based on the shifted position of the one or more of the plurality of channels.

20. The system of claim 19, wherein the more than one receiving coil or antenna of the tracking device is positioned at an end of a wire, and wherein the brachytherapy plan for administering a radiation dose to the target region comprises the seed position of the radioactive seed with respect to one of the plurality of channels and a duration at the seed position.

21. The system of claim 19, further comprising:
a marker connectable to an external portion of the target region, wherein the marker is imageable to be visible in the image and includes an electromagnetic sensor unit configured to receive the signals generated by the tracking signal generator for determination of a position and an orientation of marker; and
an imaging device that acquires the image of the target region having the marker in the image, wherein the processor is further configured to register the shifted position of the one or more of the plurality of channels based on the position measurements acquired during the movement of the tracking device, based on the position and the orientation of the marker determined from the signals received by the marker and generated by the tracking signal generator, and based on a location of the marker in the image, wherein the imaging device performs at least one of computed tomography, magnetic resonance imaging, and ultrasound imaging to acquire the image.

22. The system of claim 19, wherein the processor is further configured to determine the location of the one or more of the plurality of channels in the image based in part on image correlation algorithms that utilize one or more features shown in the image.

* * * * *